(12) United States Patent
Takaki et al.

(10) Patent No.: US 6,984,751 B2
(45) Date of Patent: Jan. 10, 2006

(54) PRODUCTION PROCESS FOR HYDROXYALKYL (METH) ACRYLATE

(75) Inventors: Hiroyuki Takaki, Himeji (JP); Tokumasa Ishida, Himeji (JP); Masahiro Uemura, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 129 days.

(21) Appl. No.: 10/633,139

(22) Filed: Aug. 1, 2003

(65) Prior Publication Data

US 2004/0030180 A1    Feb. 12, 2004

(30) Foreign Application Priority Data

Aug. 12, 2002   (JP) .............................. 2002-234630

(51) Int. Cl.
*C07C 67/26*    (2006.01)

(52) U.S. Cl. ..................................... 560/209

(58) Field of Classification Search ................. 560/224

See application file for complete search history.

(56) References Cited

U.S. PATENT DOCUMENTS 6,380,424 B1    4/2002   Yoneda et al.
2002/0198403 A1 *  12/2002   Kubo ........................ 560/231

FOREIGN PATENT DOCUMENTS

| CN | 1293185 | 5/2001 |
|---|---|---|
| DE | 101 27 939 A1 | 5/2002 |
| EP | 1 134 212 A1 | 9/2001 |
| JP | 59-44299 B2 | 10/1984 |
| JP | 59-44300 B2 | 10/1984 |
| WO | WO 02/076919 A1 | 10/2002 |
| WO | WO 02/100814 A1 | 12/2002 |

* cited by examiner

*Primary Examiner*—Paul A. Zucker

(57) ABSTRACT

There is disclosed a novel production process for a hydroxyalkyl (meth)acrylate in which: the diffusion of harmful substances due to disposal of catalysts can be reduced; and also the amount of the catalyst as used can be greatly saved in the entire production process. This production process comprises the step of carrying out a reaction between (meth)acrylic acid and an alkylene oxide in the presence of a catalyst in order to produce the hydroxyalkyl (meth)acrylate; with the production process being characterized by further comprising the step of recovering the catalyst as has been used for the reaction.

6 Claims, No Drawings

PRODUCTION PROCESS FOR HYDROXYALKYL (METH) ACRYLATE

BACKGROUND OF THE INVENTION

A. Technical Field

The present invention relates to a production process for a hydroxyalkyl (meth)acrylate, which comprises the step of carrying out a reaction between (meth)acrylic acid and an alkylene oxide in the presence of a catalyst.

B. Background Art

When a hydroxyalkyl (meth)acrylate is produced by carrying out a reaction between (meth)acrylic acid and an alkylene oxide, then a catalyst is usually used. As to the above catalyst, for example,: homogeneous catalysts (e.g. chromium compounds and iron compounds) are assumed to be suitable.

In recent years, the regulation against such as effluents and exhaust gases is becoming stricter from the viewpoint of such as environment and health. Similarly, such as disposal of catalysts is also regarded as a very serious problem from apprehension of its harmfulness. In addition, it is desired such that the amount of the catalyst as used should be saved as much as possible in the entire production process.

SUMMARY OF THE INVENTION

A. Objects of the Invention

Accordingly, an object of the present invention is to provide a production process for a hydroxyalkyl (meth)acrylate in which the diffusion of harmful substances due to disposal of catalysts can be reduced.

Also, a second object of the present invention is to provide a novel production process for a hydroxyalkyl (meth)acrylate in which the amount of the catalyst as used can be greatly saved in the entire production process.

B. Disclosure of the Invention

In order to achieve the above-mentioned first object, the present inventors have decided to recover the catalyst as has been used for the reaction in the production process for a hydroxyalkyl (meth)acrylate. Then, they have also variously devised how to recover the catalyst. As a result, they have found out an excellent method.

In order to achieve the above-mentioned second object, the present inventors have decided to recycle the recovered catalyst and have further found out a method for making the above recycling effective.

Specifically, the present inventors have found out that, in the production process for a hydroxyalkyl (meth)acrylate: (1) if the recovery of the used catalyst is carried out by bringing a residue, as left behind distilling off the objective product from the resultant reaction liquid, into contact with an ion-exchange resin and thereby causing the ion-exchange resin to adsorb the catalyst as contained in the residue, then a high recovery ratio of the catalyst can be ensured and further the catalyst is easy to recycle; (2) if the used catalyst is recovered as a solid by mixing the resultant reaction liquid and/or its residue, as left behind distilling off the objective product from the reaction liquid, with water and/or an alkali solution and then applying solid-liquid separation to the resultant mixture and further if the above solid is mixed with an acid, then the catalyst can be recovered economically in a constant recovery ratio of the catalyst, and the catalyst is easy to recycle, and also sufficient efficiency of the catalytic reaction can be performed; and (3) if the used catalyst is, as it is in a solution state, recovered by obtaining a residue as left behind distilling off the objective product from the resultant reaction liquid and further if the above residue is replenished with a fresh catalyst (e.g. unused catalyst) and then recycled for the next reaction, then the cost is so low as to be excellent in economy, and a high recovery ratio of the catalyst can be ensured, and further the catalyst can be recycled by simple operations, and also sufficient efficiency of the catalytic reaction can be performed.

The present invention has been completed via the above findings and the confirmation of their effects.

That is to say, a production process for a hydroxyalkyl (meth)acrylate, according to the present invention, comprises the step of carrying out a reaction between (meth)acrylic acid and an alkylene oxide in the presence of a catalyst in order to produce the hydroxyalkyl (meth)acrylate; with the production process being characterized by further comprising the step of recovering the catalyst as has been used for the reaction.

In the above present invention production process, it is favorable that the catalyst-recovering step includes the step of causing an ion-exchange resin to adsorb the catalyst as contained in a residue as left behind distilling off the objective hydroxyalkyl (meth)acrylate from the resultant reaction liquid. And it is more favorable that the adsorption is carried out under mixing of the residue, the ion-exchange resin, and a polar solvent. And it is still more favorable that the ion-exchange resin is a cation-exchange resin.

In the above present invention production process, it is favorable that the catalyst-recovering step includes the step of mixing a solid with an acid, wherein the solid is a product obtained by applying solid-liquid separation to a mixture of the resultant reaction liquid and/or its residue with water and/or an alkali solution, wherein the residue is a residue as left behind distilling off the objective hydroxyalkyl (meth)acrylate from the reaction liquid. And it is more favorable that: the mixture of the reaction liquid and/or its residue with the water and/or alkali solution is put in a state of high temperature; and/or the resultant mixture of the solid and the acid is put in a state of high temperature.

In the above present invention production process, it is favorable that the catalyst-recovering step includes the step of obtaining a residue as left behind distilling off the objective hydroxyalkyl (meth)acrylate from the resultant reaction liquid, with the production process further comprising the step of replenishing the resultant residue with a fresh catalyst to use the resultant mixture for the next reaction.

In the above present invention production process, it is favorable that the catalyst is a chromium compound.

These and other objects and the advantages of the present invention will be more fully apparent from the following detailed disclosure.

DETAILED DESCRIPTION OF THE INVENTION

Hereinafter, detailed descriptions are given about the production process for a hydroxyalkyl (meth)acrylate according to the present invention (which may hereinafter be referred to as the present invention production process). However, the scope of the present invention is not bound to these descriptions. And other than the following illustrations can also be carried out in the form of appropriate modifications of the following illustrations within the scope not departing from the spirit of the present invention.

Hereinafter, first of all, descriptions are given about general modes for carrying out the production process for a hydroxyalkyl (meth)acrylate for carrying out the present invention. Thereafter, detailed descriptions are given about the recovery of the used catalyst by which the present invention is characterized. However, the present invention is not limited to these descriptions.

In the present invention production process, that is, in the production process which comprises the step of carrying out the reaction between the (meth)acrylic acid and the alkylene oxide in the presence of the catalyst in order to obtain the hydroxyalkyl (meth)acrylate, specifically, it is general that: the reaction is allowed to run by fitly supplying the catalyst, the (meth)acrylic acid, and the alkylene oxide into a reactor, and then the reaction is finished when the amount of the residual (meth)acrylic acid in the reaction liquid has decreased to a desired amount. Incidentally, the above reaction is an exothermic reaction, and it is herein provided that: the reaction should start when the (meth)acrylic acid and the alkylene oxide have come to coexist in the presence of the catalyst, and then the reaction should be finished by dropping the temperature of the reaction liquid to lower than a set definite reaction temperature by such as cooling.

In the present invention production process, as to the quantitative relation between the amount of the entire supply of the (meth)acrylic acid and the amount of the entire supply of the alkylene oxide (relation between the amounts of raw materials as charged), the alkylene oxide is favorably not smaller than 1 mol, more favorably in the range of 1.0 to 10 mols, still more favorably 1.0 to 5.0 mols, particularly favorably 1.0 to 3.0 mols, most favorably 1.0 to 2.0 mols, relative to 1 mol of the (meth)acrylic acid. In the case where the amount of the entire supply of the alkylene oxide is smaller than 1.0 mol, there is a possibility that: the reaction may be so difficult to run that the reaction conversion is lowered, and that by-products increase. In addition, in the case where the amount of the entire supply of the alkylene oxide is too large (particularly, larger than 10 mols), there may be economical disadvantages in that such as step of recovering the alkylene oxide is needed.

The (meth)acrylic acid usable in the present invention production process refers to acrylic acid and/or methacrylic acid.

The alkylene oxide usable in the present invention production process is favorably an alkylene oxide having 2 to 6 carbon atoms, more favorably 2 to 4 carbon atoms. Above all, ethylene oxide, propylene oxide, and butylene oxide are favorable, and the ethylene oxide and the propylene oxide are preferable.

As to the method (order) for charging the aforementioned (meth)acrylic acid and alkylene oxide, usually, it is general that: a portion or the entirety of the (meth)acrylic acid is initially charged into the reactor, and then thereto the alkylene oxide or both the alkylene oxide and the residual (meth)acrylic acid are supplied. However, there is no limitation thereto. For example, a portion or the entirety of the alkylene oxide may be initially charged.

The supply of the aforementioned (meth)acrylic acid and alkylene oxide may be carried out either by lump addition or by gradual addition (continuous addition and/or intermittent addition). However, the lump addition is favorable for the portions being initially charged, and the gradual addition is favorable for the portions being supplied thereafter. Incidentally, the continuous addition refers to a mode of carrying out the addition little by little continuously, and the intermittent addition refers to a mode of carrying out the addition pulsewise or intermittently with the addition being divided into any number of times. Besides, in the case of carrying out the addition continuously, the addition may be allowed to go on, with the addition rate left constant until the end of the addition, or with the rate changed at least once midway, or while the rate itself is varied continuously and optionally.

The present invention production process may be carried out either in a batch manner or in a continuous manner, and either of these manners can fitly be selected.

In the case where the reaction is carried out in a batch manner, usually, the reaction is carried out by supplying a liquid alkylene oxide into the (meth)acrylic acid. The alkylene oxide may be supplied after the (meth)acrylic acid has been dissolved into a solvent. Hereupon, as is aforementioned, the alkylene oxide may be added to the (meth)acrylic acid either in a lump or gradually. In the case where the alkylene oxide is gradually added, it is also possible that: as is often the case with this kind of reaction, the reaction is continued still after the supply of the alkylene oxide, thereby carrying out so-called aging to complete the reaction.

In the case where the reaction is carried out in a continuous manner, usually, the reaction is carried out by continuously adding the (meth)acrylic acid and the liquid alkylene oxide into a reactor such as a tubular or tank reactor and continuously extracting the resultant reaction liquid from the reactor. In this case, there may be adopted a mode such that the reaction liquid is partially circulated.

When the (meth)acrylic acid and the alkylene oxide are added, they may be added at ordinary temperature, or may be added after having beforehand been heated to a desired temperature in order not to change the temperature in the system at that point of time.

In the case where both the (meth)acrylic acid and the alkylene oxide are added at the same time, they may be added from their respective addition lines, or they may be added to the reactor after having beforehand been mixed by using such as piping, a line mixer, or a mixing tank before being added to the reactor. However, in the case where they are added from their respective addition lines, there is a possibility that the inclination of the molar ratio between the alkylene oxide and the (meth)acrylic acid may occur in the system. Therefore, it is favorable that they are added to the reactor after having beforehand been mixed before being added to the reactor. Incidentally, in the case where they are added from their respective addition lines, then such as the mode for the addition (e.g. whether it is lump addition or gradual addition), the temperature of the raw material being added, and the addition rate do not necessarily need to be the same between the raw materials.

There is no limitation on the time as required for finishing charging the amount of the entire supplies of the aforementioned (meth)acrylic acid and alkylene oxide. The above time may fitly be set in consideration of such as the reaction progress conditions and the productivity.

As to the catalyst usable in the present invention production process, there is no limitation, but there can be cited all homogeneous catalysts soluble in the aforementioned reaction liquid. However, favorable examples thereof include catalysts which are homogeneous catalysts soluble in the aforementioned reaction liquid and include at least one member selected from the group consisting of a chromium (Cr) compound, an iron (Fe) compound, an yttrium (Y) compound, a lanthanum (La) compound, a cerium (Ce) compound, a tungsten (W) compound, a zirconium (Zr) compound, a titanium (Ti) compound, a vanadium (V) compound, a phosphorus (P) compound, an aluminum (Al) compound, and a molybdenum (Mo) compound. More favorable of the above are catalysts that include the chromium (Cr) compound and/or the iron (Fe) compound and are homogeneous catalysts soluble in the aforementioned reaction liquid. Still more favorable are catalysts that include the chromium (Cr) compound and are homogeneous catalysts soluble in the aforementioned reaction liquid.

There is no limitation on the chromium (Cr) compound if it is a compound that contains a chromium (Cr) atom in its molecule and is soluble in the aforementioned reaction liquid. Examples thereof include chromium chloride, chromium acetylacetonate, chromium formate, chromium acetate, chromium acrylate, chromium methacrylate, sodium bichromate, and chromium dibutyldithiocarbamate.

There is no limitation on the iron (Fe) compound if it is a compound that contains an iron (Fe) atom in its molecule and is soluble in the aforementioned reaction liquid. Examples thereof include iron powders, iron chloride, iron formate, iron acetate, iron acrylate, and iron methacrylate.

There is no limitation on the yttrium (Y) compound if it is a compound that contains an yttrium (Y) atom in its molecule and is soluble in the aforementioned reaction liquid. Examples thereof include yttrium acetylacetonate, yttrium chloride, yttrium acetate, yttrium nitrate, yttrium sulfate, yttrium acrylate, and yttrium methacrylate.

There is no limitation on the lanthanum (La) compound if it is a compound that contains a lanthanum (La) atom in its molecule and is soluble in the aforementioned reaction liquid. Examples thereof include lanthanum acetylacetonate, lanthanum chloride, lanthanum acetate, lanthanum nitrate, lanthanum sulfate, lanthanum acrylate, and lanthanum methacrylate.

There is no limitation on the cerium (Ce) compound if it is a compound that contains a cerium (Ce) atom in its molecule and is soluble in the aforementioned reaction liquid. Examples thereof include cerium acetylacetonate, cerium chloride, cerium acetate, cerium nitrate, cerium sulfate, cerium acrylate, and cerium methacrylate.

There is no limitation on the tungsten (W) compound if it is a compound that contains a tungsten (W) atom in its molecule and is soluble in the aforementioned reaction liquid. Examples thereof include tungsten chloride, tungsten acrylate, and tungsten methacrylate.

There is no limitation on the zirconium (Zr) compound if it is a compound that contains a zirconium (Zr) atom in its molecule and is soluble in the aforementioned reaction liquid. Examples thereof include zirconium acetylacetonate, zirconium chloride, zirconium acetate, zirconium nitrate, zirconium sulfate, zirconium acrylate, zirconium methacrylate, zirconium butoxide, zirconium propoxide, zirconyl chloride, zirconyl acetate, zirconyl nitrate, zirconyl acrylate, and zirconyl methacrylate.

There is no limitation on the titanium (Ti) compound if it is a compound that contains a titanium (Ti) atom in its molecule and is soluble in the aforementioned reaction liquid. Examples thereof include titanium chloride, titanium nitrate, titanium sulfate, titanium methoxide, titanium ethoxide, titanium propoxide, titanium isopropoxide, titanium acrylate, and titanium methacrylate.

There is no limitation on the vanadium (V) compound if it is a compound that contains a vanadium (V) atom in its molecule and is soluble in the aforementioned reaction liquid. Examples thereof include vanadium acetylacetonate, vanadium chloride, vanadium naphthenate, vanadium acrylate, and vanadium methacrylate.

There is no limitation on the phosphorus (P) compound if it is a compound that contains a phosphorus (P) atom in its molecule and is soluble in the aforementioned reaction liquid. Examples thereof include: alkylphosphines, such as trimethylphosphine, tributylphosphine, trioctylphosphine, triphenylphosphine, tritolylphosphine, and 1,2-bis(diphenylphosphine)ethane; and quaternary phosphonium salts such as (meth)acrylate salts of the above alkylphosphines.

There is no limitation on the aluminum (Al) compound if it is a compound that contains an aluminum (Al) atom in its molecule and is soluble in the aforementioned reaction liquid. Examples thereof include aluminum acetylacetonate, aluminum chloride, aluminum acetate, aluminum nitrate, aluminum sulfate, aluminum ethoxide, aluminum isopropoxide, aluminum acrylate, and aluminum methacrylate.

There is no limitation on the molybdenum (Mo) compound if it is a compound that contains a molybdenum (Mo) atom in its molecule and is soluble in the aforementioned reaction liquid. Examples thereof include molybdenum chloride, molybdenum acetate, molybdenum acrylate, and molybdenum methacrylate.

In the present invention production process, an amine compound may further be used as the catalyst together with a catalyst which is a homogeneous catalyst soluble in the aforementioned reaction liquid and includes at least one member selected from the group consisting of the chromium (Cr) compound, the iron (Fe) compound, the zirconium (Zr) compound, the titanium (Ti) compound, the vanadium (V) compound, the phosphorus (P) compound, the aluminum (Al) compound, and the molybdenum (Mo) compound as mentioned above.

There is no limitation on the above amine compound if it is a compound that contains an amine functional group in its molecule. Examples thereof include: homogeneous amine compounds, such as trialkylamines, cyclic amines (e.g. pyridine), and their quaternary salts.

In the present invention, when the above amine compound is used together as the catalyst, there are obtained effects such that: the synergistic effect is seen as to the catalytic activity, and the reaction conversion is raised, and further the reaction selectivity is also raised.

There is no limitation on the amount of the catalyst as used in the present invention production process. For example, in the case of also using the catalyst which includes at least one member selected from among such as the chromium (Cr) compounds as enumerated above and is a homogeneous catalyst soluble in the aforementioned reaction liquid, then the amount of the catalyst as used is favorably in the range of 0.01 to 10 mol %, more favorably 0.02 to 5 mol %, still more favorably 0.04 to 3 mol %, relative to the raw (meth)acrylic acid. In the case where the above amount as used is smaller than 0.01 mol %, there is a possibility that: the reaction rate may be so slow that the reaction time is prolonged, resulting in low productivity. In the case where the above amount as used is larger than 10 mol %, there is a possibility that the reaction selectivity of by-products may rise.

In the case of also using a catalyst comprising the joint use of the homogeneous amine compound with the catalyst which includes at least one member selected from among such as the chromium (Cr) compounds as enumerated above and is a homogeneous catalyst soluble in the aforementioned reaction liquid, then there is no limitation on the amount of the catalyst as used, wherein this amount as used is favorably in the range of 0.01 to 10 mol %, more favorably 0.02 to 5 mol %, still more favorably 0.04 to 3 mol %, relative to the raw (meth)acrylic acid. In the case where the above amount as used is smaller than 0.01 mol %, there is a possibility that: the reaction rate may be so slow that the reaction time is prolonged, resulting in low productivity. In the case where the above amount as used is larger than 10 mol %, there is a possibility that the reaction selectivity of by-products may rise.

As to the aforementioned catalyst, it is general that its entirety to be used is beforehand charged into the reactor. However, there is no limitation thereto. For example, a portion of the entirety to be used may be initially charged into the reactor, and thereafter the rest may be additionally supplied thereinto halfway through the progress of the reaction. Besides, in the case where the aforementioned catalyst is a homogeneous catalyst, the catalyst may be charged or supplied into the reactor after having beforehand been dissolved into either of both raw materials. For example, in the case where the catalyst is initially charged, the catalyst may be charged into the reactor after having beforehand been dissolved into a raw material (which is to be initially charged) in a dissolution tank different from the reactor.

In the case where the reaction is carried out in a batch manner, it is favorable that: the aforementioned catalyst is beforehand charged into the (meth)acrylic acid, the hydroxyalkyl (meth)acrylate, the solvent, or their mixed liquids, and thereafter the alkylene oxide is introduced. Besides, in the case where the (meth)acrylic acid is gradually added, the catalyst may be added together with the (meth)acrylic acid by beforehand charging portions of the catalyst into the (meth)acrylic acid which will be gradually added.

In the case where the reaction is carried out in a continuous manner, it is favorable that: the aforementioned catalyst is beforehand charged into the (meth)acrylic acid, the hydroxyalkyl (meth)acrylate, the solvent, or their mixed liquids, and thereafter the resultant mixture is continuously added into the reactor. The catalyst may continuously be extracted together with the resultant reaction liquid.

When the aforementioned reaction is carried out in the present invention production process, polymerization inhibitors may be added into the reaction system, if necessary. There is no limitation on the polymerization inhibitors, and the polymerization inhibitors are usable if they are generally industrially used. Examples thereof include: phenol compounds, such as hydroquinone, methylhydroquinone, tert-butylhydroquinone, 2,6-di-tert-butylhydroquinone, 2,5-di-tert-butylhydroquinone, 2,4-dimethyl-6-tert-butylphenol, and hydroquinone monomethyl ether; para-phenylenediamines, such as N-isopropyl-N'-phenyl-para-phenylenediamine, N-(1,3-dimethylbutyl)-N'-phenyl-para-phenylenediamine, N-(1-methylheptyl)-N'-phenyl-para-phenylenediamine, N,N'-diphenyl-para-phenylenediamine, and N,N'-di-2-naphthyl-para-phenylenediamine; amine compounds such as thiodiphenylamine and phenothiazine; copper dialkyldithiocarbamates, such as copper dibutyldithiocarbamate, copper diethyldithiocarbamate, and copper dimethyldithiocarbamate; and N-oxyl compounds, such as 2,2,4,4-tetramethylazetidine-1-oxyl, 2,2-dimethyl-4,4-dipropylazetidine-1-oxyl, 2,2,5,5-tetramethylpyrrolidine-1-oxyl, 2,2,5,5-tetramethyl-3-oxopyrrolidine-1-oxyl, 2,2,6,6-tetramethylpiperidine-1-oxyl, 4-hydroxy-2,2,6,6-tetramethylpiperidine-1-oxyl, 6-aza-7,7-dimethyl-spiro(4,5)decane-6-oxyl, 2,2,6,6-tetramethyl-4-acetoxypiperidine-1-oxyl, 2,2,6,6-tetramethyl-4-benzoyloxypiperidine-1-oxyl, and 4,4',4"-tris-(2,2,6,6-tetramethylpiperidine-1-oxyl) phosphite. These polymerization inhibitors may be used either alone respectively or in combinations with each other.

In the case of using the aforementioned polymerization inhibitor, its amount as added is favorably in the range of 0.0001 to 1 weight %, more favorably 0.001 to 0.5 weight %, relative to the amount of the entire supply of the raw (meth)acrylic acid. Besides, there is no limitation on when to add the polymerization inhibitor. It is favorable to initially add the polymerization inhibitor into the reactor together with the component which is to be initially charged.

When the aforementioned reaction is carried out, the reaction may be carried out in the presence of a solvent, if necessary, for the purpose of such as mildly running the reaction. As to the solvent, specifically for example, there can be used one or more kinds of conventional solvents such as toluene, xylene, heptane, and octane.

The temperature of the aforementioned reaction is generally favorably in the range of 40 to 130° C., more favorably 50 to 120° C., still more favorably 50 to 110° C., particularly favorably 50 to 100° C. In the case where the above reaction temperature is lower than 40° C., there is a possibility that: the reaction rate may remarkably slow, so that the reaction time may be prolonged, resulting in low productivity. In the case where the above reaction temperature is higher than 130° C., there is a possibility that a diester and/or diaddition product may easily form as a by-product.

Though depending upon the kinds and/or ratios of the raw materials as used, yet the pressure in the reactor during the aforementioned reaction is generally favorably set so that the reaction can be carried out under increased pressure.

When to end the aforementioned reaction (in other words, when to begin quenching the reaction) may be judged to be when the residual unreacted (meth)acrylic acid has disappeared sufficiently. Specifically, it is favorable to begin the quenching when the amount of the unreacted (meth)acrylic acid has decreased to not larger than 0.2 weight %, more favorably not larger than 0.1 weight %.

In order to obtain the objective hydroxyalkyl (meth)acrylate, the purification (e.g. distillation) as usually carried out in this kind of reaction may be carried out after the end of the aforementioned reaction, thereby recovering the objective hydroxyalkyl (meth)acrylate. For example, the distillation may be carried out under a pressure of 1 to 50 hPa (favorably 1 to 20 hPa) in the temperature range of 50 to 120° C. (favorably 60 to 100° C.).

When the objective hydroxyalkyl (meth)acrylate is obtained, it is favorable to add a diester inhibitor after the end of the aforementioned reaction. This addition can also effectively inhibit the side production of the diester (which progresses after the end of the reaction) and further can reduce the amount of the diester. Examples of the diester inhibitor include: carboxylic acids and their anhydrides, such as oxalic acid, oxalic anhydride, malonic acid, succinic acid, succinic anhydride, fumaric acid, maleic acid, maleic anhydride, salicylic acid, octanoic acid, adipic acid, sebacic acid, tetradecanedicarboxylic acid, 1,2,4-butanetricarboxylic acid, 1,3,6-hexanetricarboxylic acid, 1,2,3,4-butanetetracarboxylic acid, 1,2,3,4-pentanetetracarboxylic acid, 1,6,7,12-dodecanetetracarboxylic acid, benzoic acid, o-toluic acid, m-toluic acid, p-toluic acid, phthalic acid, phthalic anhydride, isophthalic acid, terephthalic acid, 2,6-naphthalenedicarboxylic acid, pyromellitic acid, pyromellitic anhydride, trimellitic acid, trimellitic anhydride, 1,2,4-benzenetricarboxylic acid, 1,4,5,8-naphthalenetetracarboxylic acid, 1,3,5,7-naphthalenetetracarboxylic acid, and polyacrylic acid; polyhydric alcohols, such as glycerin, diethylene glycol, trimethylolpropane, cresol, 1,2,6-hexanetriol, pentaerythritol, dipentaerythritol, 2,3,4,5-tetrahydroxyhexane, xylitol, mannitol, catechol, resorcin, 2,6-dihydroxytoluene, tert-butylcatechol, pyrogallol, 2,4-bis(hydroxymethyl)phenol, 1,2,4-trihydroxybenzene, 1,3,5-trihydroxybenzene, 2,4,6-tris(hydroxymethyl)phenol, and 1,2,4,5-tetrahydroxybenzene; and metal-chelating agents, such as ethylenediaminetetraacetic acid, ethylenediaminetetrapropionic acid, nitrilotriacetic acid, iminodiacetic acid, 1,2-diaminocyclohexanetetraacetic acid, acetylacetone, cupferron, oxine, benzidine, and diethyldithiocarbamic acid. These diester inhibitors may be used either alone respectively or in combinations with each other.

In the case of using the aforementioned diester inhibitor, its amount as added is favorably in the range of 0.1 to 10 mols, more favorably 0.5 to 5 mols, per 1 mol of the aforementioned catalyst. In the case where the above amount as added is smaller than 0.1 mol per 1 mol of the catalyst, there is a possibility that the effect of inhibiting the side production of the diester may not be displayed sufficiently. In the case where the above amount as added is larger than 10 mols, there is a possibility that the added diester inhibitor may deteriorate the product purity. Particularly, in the case of using the carboxylic acids, there is a possibility that the content of the acid components in the product as obtained may increase. Besides, there is no limitation on when to add the diester inhibitor if the addition is carried out after the end of the reaction. For example, it is favorable that the addition is carried out at once or with the addition divided into a plural number of times, for example, immediately after the stop of the reaction (the beginning of the quenching), at the initiation of the distillation, or during the distillation, and it is more favorable to carry out the addition immediately after the stop of the reaction.

In the present invention production process, the resultant crude hydroxyalkyl (meth)acrylate may further be purified when the occasion demands. There is no limitation on the purification method therefor. Examples thereof include purification by distillation, more specifically, distillation involving the use of such as conventional distillation columns and rectifying columns (e.g. packed columns, bubble cap columns, perforated-plate columns). However, there is no especial limitation thereto. In addition, other purification means may be used jointly with the distillation purification. In addition, the aforementioned polymerization inhibitors can fitly be used also when the purification is carried out.

The present invention production process is characterized by further comprising the step of recovering the catalyst as has been used for the aforementioned reaction between the (meth)acrylic acid and the alkylene oxide.

There is no limitation on the method for the aforementioned recovery of the catalyst if it is such a method as can easily achieve the aforementioned object. And publicly known recovery methods can also be adopted. However, in the present invention, it is favorable to carry out the recovery by the aforementioned methods (1) to (3).

Thus, hereinafter, detailed descriptions are given about these methods (1) to (3).

<Method (1)>:

The method (1) is a method in which the catalyst-recovering step includes the step (A) of causing an ion-exchange resin to adsorb the catalyst as contained in a residue as left behind distilling off the objective hydroxyalkyl (meth)acrylate from the resultant reaction liquid.

In the method (1), for example, it is favorable to bring the aforementioned residue into contact with the ion-exchange resin and thereby cause the ion-exchange resin to adsorb the used catalyst as contained in the aforementioned residue. Thus, the target which is such as brought into contact with the ion-exchange resin for the purpose of the aforementioned adsorption is a residue as left behind distilling off the entirety or a portion of the objective hydroxyalkyl (meth) acrylate from the reaction liquid resultant from the aforementioned reaction. However, the above target is favorably a residue as left behind distilling off substantially the entirety. If the residue is targeted and if the ion-exchange resin is caused to adsorb the catalyst as contained in the above residue, then the above method becomes a still more excellent method in that such as the adsorption efficiency, in other words, the recovery ratio of the catalyst, and/or the product purity resultant from the distillation can be enhanced, when compared with the case where a reaction liquid from which the objective product has not yet been distilled off is targeted for the contact.

Incidentally, the above residue may be referred to as distillation residue or boiler residue and, generally, it is often liquid (e.g. tarry). However, the above residue is not limited to such, but, in the case where the residue is obtained in a solid state without flowability, such a residue is also included conceptually.

As to the ion-exchange resin as used in the method (1), it can fitly be selected according to such as the kind of the catalyst to be recovered. Therefore, there is no limitation. Examples thereof include: cation-exchange resins such as strongly acidic cation-exchange resins and weakly acidic cation-exchange resins; anion-exchange resins such as strongly basic anion-exchange resins and weakly basic anion-exchange resins; and synthetic adsorbing agents. Above all, the cation-exchange resins are favorable, and the strongly acidic cation-exchange resins are more favorable, in that: they display a high catalyst-adsorbing ratio, and are so inexpensive as to be economically excellent, and involve little deterioration in the adsorbing and desorbing abilities.

Generally, the cation-exchange resins are resins which can exchange cations such as sodium ion and calcium ion, and are classified into the strongly acidic cation-exchange resins and the weakly acidic cation-exchange resins according to the strength of the acidity of their exchange groups. For example, when typical exchange groups are compared as to the strength of their acidity, its order is as follows:

R—SO$_3$H>R—CH$_2$SO$_3$H>R—COOH>R—OH (wherein R denotes the parent body of the ion-exchange resin).

In addition, the pH ranges (effective pH ranges) of the liquid phase in which these exchange groups can sufficiently make ion-exchange reactions are as follows: not less than 2.0 for R—SO$_3$H; not less than 4.0 for R—CH$_2$SO$_3$H; not less than 6.0 for R—COOH; and not less than 10.0 for R—OH.

Based on the above findings, in the method (1), the strongly acidic cation-exchange resins refer to those which include at least the pH range of not less than 4.0 as the above effective pH range (wherein the lower limit value of the above effective pH range is not more than 4.0), and examples thereof include those which have such as a sulfonic acid group. The weakly acidic cation-exchange resins refer to those which are cation-exchange resins other than the above strongly acidic cation-exchange resins and include at least the pH range of not less than 10.0 as the above effective pH range (wherein the lower limit value of the above effective pH range is more than 4.0 but not more than 10.0), and examples thereof include those which have such as a carboxyl group, a phenolic hydroxyl group, a phosphonic acid group, and an arsono group.

As to the shape and form of the ion-exchange resin, they can fitly be selected. Therefore, there is no limitation.

In the method (1), as to the method and mode for the aforementioned adsorption, they can fitly be selected according to such as: the kind of the catalyst to be recovered; the state of the residue; and the shape of the ion-exchange resin. Therefore, there is no limitation. Examples thereof include: a method in which the residue and the ion-exchange resin are stir-mixed together; and a method in which the ion-exchange resin is packed into a tube such as a SUS-made one, and then the residue is passed through the packed ion-exchange resin. Above all, the latter method is preferable in that: it is easy to separate the residue and the ion-exchange resin from each other; and the apparatus can be compacted.

As to the amount of the ion-exchange resin as used, it can fitly be selected according to such as: the kind and amount of the catalyst to be recovered from the residue; and the conditions of the use of the catalyst. Therefore, there is no limitation. For example, the above amount as used is favorably in the range of 2 to 30 weight %, more favorably 3 to 25 weight %, still more favorably 5 to 20 weight %, relative to the weight of the residue. In the case where the above amount as used is smaller than 2 weight %, there is a possibility that the entire catalyst in the residue cannot be adsorbed. In the case where the above amount as used is larger than 30 weight %, there may be economical disadvantages in that the amount of the ion-exchange resin is too large.

In the method (1), it is favorable that, in preparation for the aforementioned adsorption, the residue is beforehand mixed with a polar solvent to obtain a mixed solution. By carrying out such mixing, the ratio of the adsorption of the catalyst onto the ion-exchange resin can effectively be enhanced, so that a high recovery ratio of the catalyst can be achieved.

A particularly favorable mode for the adsorption by use of the polar solvent is a mode such that the adsorption is carried out under mixing of the residue, the ion-exchange resin, and the polar solvent. By adopting this mode, there can be obtained excellent effects such that the ratio of the adsorption of the catalyst in the residue onto the ion-exchange resin can be enhanced.

As to the above polar solvent, if it is such a solvent as produces the above effects, then it can fitly be selected and is therefore not limited. For example, there can be used at least one member selected from the group consisting of such as water, methanol, ethanol, propanol, acetone, formic acid, acetic acid, acrylic acid, methacrylic acid, DMF, and ethylene glycol. Above all, in point of the adsorption ratio and the solvent cost, water, methanol and acetone are favorable, and water and methanol are more favorable.

In the method (1), as to the temperature in the aforementioned adsorption, that is, the temperature during the use of the ion-exchange resin, it can fitly be selected according to such as: the kind of the catalyst to be recovered; and the conditions of the use of the catalyst. Therefore, there is no limitation. For example, the above temperature is favorably in the range of 60 to 90° C., more favorably 70 to 90° C., still more favorably 75 to 85° C. In the case where the above temperature is lower than 60° C., there is a possibility that the ratio of the adsorption of the catalyst onto the ion-exchange resin may be so insufficient as to be inferior also economically. In the case where the above temperature is higher than 90° C., there is a possibility that: the polar solvent may boil, or the residue may polymerize.

In the method (1), as to the duration of the aforementioned adsorption, that is, the duration of the use of the ion-exchange resin, it can fitly be selected according to such as: the kind of the catalyst to be recovered; and the conditions of the use of the catalyst. Therefore, there is no limitation. For example, the above duration is favorably in the range of 0.5 to 24 h, more favorably 1 to 10 h, still more favorably 3 to 5 h. In the case where the above duration is shorter than 0.5 h, there is a possibility that the ratio of the adsorption of the catalyst onto the ion-exchange resin cannot sufficiently be obtained. In the case where the above duration is longer than 24 h, there is a possibility that: the productivity may be so low as to be inferior economically.

The method (1) may further include another step besides the aforementioned step (A). For example, the method (1) can include such as the step of desorb the catalyst from the catalyst-adsorbed ion-exchange resin as obtained in the aforementioned step (A). By this desorption step, the catalyst can be recovered as a solid, and the recovered catalyst can, as it is, be recycled for the reaction between the (meth)acrylic acid and the alkylene oxide. In addition, the catalyst-adsorbed ion-exchange resin may, as it is, be recycled for the aforementioned reaction. Incidentally, the means for the aforementioned desorption is not limited. For example, means such as of passing an aqueous sodium chloride solution through the resin to thereby elute the catalyst can be adopted. The eluted catalyst above can be powdered by treating the eluate by methods such as reduced-pressure drying, reduced-pressure distillation and spray-drying, and thus can be recovered in the form usable for the next reaction.

The method (1) may still further include another step in which a mixture of the catalyst-adsorbed ion-exchange resin (as obtained in the aforementioned step (A)) and the aforementioned residue is used instead of the reaction liquid and/or its residue in the step (I) as included in the step (B) of the below-mentioned method (2), wherein the above reaction liquid and/or its residue is such as referred to in the step (I). The catalyst is in a state of remaining adsorbed to the ion-exchange resin, but there can be obtained the same effects as in the method (2). Furthermore, if the aforementioned means for the desorption is applied to the catalyst-adsorbed ion-exchange resin as processed by the step (B) of the method (2), then only the catalyst can be recovered.

<Method (2)>:

The method (2) is a method in which the catalyst-recovering step includes the step (B) of mixing a solid with an acid, wherein the solid is a product obtained by applying solid-liquid separation to a mixture of the resultant reaction liquid and/or its residue with water and/or an alkali solution, wherein the residue is a residue as left behind distilling off the objective hydroxyalkyl (meth)acrylate from the reaction liquid.

The step (B) as referred to in this method (2), first, needs the step (I) of mixing the resultant reaction liquid and/or its residue with water and/or an alkali solution, wherein the residue is a residue as left behind recovery of the objective hydroxyalkyl (meth)acrylate from the reaction liquid. It seems that: in the step (I), the catalyst as has been used for the aforementioned reaction is converted into a hydroxide (e.g. chromium hydroxide) (which is insoluble in an aqueous solvent) by mixing the aforementioned residue with the water and/or the alkali solution. As a result, there is formed a white insoluble product (solid) in the mixture resultant from this step (I).

In the aforementioned step (I), there is no limitation on the target which is mixed with the water and/or alkali solution, if this target contains the used catalyst. Specifically, this target may be either a reaction liquid containing the objective hydroxyalkyl (meth)acrylate (reaction liquid from which the objective hydroxyalkyl (meth)acrylate has not yet been distilled off) or the residue as left behind distilling off the entirety or a portion of the objective hydroxyalkyl (meth)acrylate from the reaction liquid. Incidentally, as to the form and conception of the above residue, the same explanation as of the aforementioned method (1) is applicable thereto.

Examples of the alkali solution as used in the aforementioned step (I) include aqueous solutions or alcoholic solutions (the alcohol is favorably a high-water-soluble alcohol such as methanol, ethanol, or ethylene glycol) of alkaline metal hydroxides (e.g. sodium hydroxide and potassium hydroxide), alkaline earth metal hydroxides (e.g. magnesium hydroxide and calcium hydroxide), and alkaline compounds (e.g. ammonia and amines). Particularly, when substances having low water solubility such as the magnesium hydroxide are used, there are advantages in that the particle sizes of the resultant precipitate (e.g. chromium hydroxide) are so large that the precipitate is easy to separate in the next step (II) (for example, in the case of carrying out filtration, the filtration performance is so good that the filtration time is shortened). Incidentally, the alkali solution may be used either alone respectively or in combinations with each other.

The concentration of the aforementioned alkali solution may fitly be set according to the composition of the aforementioned reaction liquid and/or its residue (e.g. the amount of the catalyst as contained in the aforementioned reaction liquid and/or its residue (namely, the theoretical amount as calculated from the amount of the catalyst as used when the hydroxyalkyl (meth)acrylate is produced) and the amount of the ester as contained in the aforementioned reaction liquid and/or its residue) and/or according to the amount of the alkali solution as used. Therefore, there is no limitation. For example, in the case where the chromium compound is used as the catalyst and where a residue that is left behind distillation in a distillate ratio of 90% and has a catalyst (chromium) content of 0.5 weight % is used, then it is favorable to adjust the concentration so that the alkaline compound content can be in the range of 5 to 40 weight % relative to the above residue.

There is no limitation on the amount of the water and/or alkali solution as used in the aforementioned step (I) if this amount is in such a range that the hydroxide being formed can precipitate as an insoluble product in a mixture (mixed solution) as obtained by mixing the aforementioned reaction liquid and/or its residue with the water and/or the alkali solution. The above amount may fitly be set in consideration of: the solubility of the hydroxide to the above mixed solution (the composition of the aforementioned reaction liquid and/or its residue (e.g. the amount of the ester as contained in the aforementioned reaction liquid and/or its residue) and/or the composition of the water and/or alkali solution); and/or the amount of the hydroxide (=the theoretical amount as calculated from the amount of the catalyst as used when the hydroxyalkyl (meth)acrylate is produced). For example, in the case where the chromium compound is used as the catalyst and where the residue that is left behind distillation in a distillate ratio of 90% and has a catalyst (chromium) content of 0.5 weight % is mixed with a 10 weight % aqueous sodium hydroxide solution as the water and/or alkali solution, then it is favorable that the amount of the water and/or alkali solution as used is adjusted in the range of 25 to 500 weight % relative to the above residue.

In the aforementioned step (I), it is favorable that the mixture as obtained by mixing the aforementioned reaction liquid and/or its residue and the aforementioned water and/or alkali solution together is put in a state of high temperature. Hereupon, putting the mixture in the state of high temperature refers to: preheating either one or both of the aforementioned reaction liquid and/or its residue and the aforementioned water and/or alkali solution before they are mixed together, and then mixing them together; or heating the resultant mixture at the same time as or after mixing the aforementioned reaction liquid and/or its residue and the aforementioned water and/or alkali solution together. Thereby, the recovery efficiency of the catalyst can be enhanced. There is no limitation on the conditions for putting the mixture in the state of high temperature (heating conditions). The conditions will do, for example, if they are such that the mixture is maintained in the temperature range of 40 to 100° C. for 0.5 to 5 hours. Incidentally, in the case where the mixture is not put in the state of high temperature (the heating is not carried out), it is favorable to age (leave) the mixture at room temperature for 2 to 24 hours after the mixing.

After the aforementioned step (I), the step (B) as referred to in the method (2) needs the step (II) of applying solid-liquid separation to the mixture resultant from the step (I). The solid as separated in the aforementioned step (II) is presumed to be a hydroxide (e.g. chromium hydroxide) and will be subjected to the subsequent step (III).

There is no limitation on the means for the solid-liquid separation in the aforementioned step (II). This means will do if it is a conventional means such as filtration or decantation. Favorably, it is desirable to carry out the separation in such a manner that the volatile matter of the separated solid will not be more than 30%. In addition, if, in the case of using the alkali solution in the aforementioned step (I), the alkali remains such as adhering to the solid as separated in the aforementioned step (II), then this alkali may exercise an bad influence such as formation of by-products in the subsequent step (III). Therefore, after the separation, it is favorable to wash the separated solid with a solvent having high solubility to the alkali (e.g. water and methanol). Hereupon, it is more desirable to repeat the washing until the pH of the solvent decreases to not more than 9, favorably not more than 8, as a result of the washing.

After the aforementioned step (II), the step (B) as referred to in the method (2) needs the step (III) of mixing the solid with an acid, wherein the solid is a solid as separated in the step (II). It is presumed that, in the aforementioned step (III), as a result of the mixing of the aforementioned solid (which is presumed to be a hydroxide (e.g. chromium hydroxide)) and the acid, the hydroxide is converted into a salt of the acid as used. Hereupon, if the above hydroxide is, for example, chromium hydroxide, then this chromium hydroxide (which is usually white) turns dark green that is peculiar to chromium salts.

Examples of the acid as used in the aforementioned step (III) include: inorganic acids, such as hydrochloric acid, nitric acid, and sulfuric acid; and organic acids, such as formic acid, acetic acid, (meth)acrylic acid, octanoic acid, oxalic acid, succinic acid, maleic acid, and salicylic acid. In the present invention, of these acids, the (meth)acrylic acid that are reactants are particularly preferable. Incidentally, the acids may be used either alone respectively or in combinations with each other. Hereupon, in the case where the reactant is used as the acid referred to in the step (III), the mixture resultant from the step (III) can, as it is, be used for the reaction system between the (meth)acrylic acid and the alkylene oxide.

There is no limitation on the amount of the acid as used in the aforementioned step (III). For example, it is favorable that the molar ratio of the acid to the theoretical amount as calculated from the amount of the catalyst as used when the hydroxyalkyl (meth)acrylate is produced is adjusted in the range of 1 to 20.

In the aforementioned step (III), it is favorable that the mixture as obtained by mixing the aforementioned solid and the aforementioned acid together is put in a state of high temperature. Hereupon, putting the mixture in the state of high temperature refers to: preheating the acid before the mixing, and then carrying out the mixing; or heating the resultant mixture at the same time as or after mixing the aforementioned solid and the aforementioned acid together. Thereby, the recovery efficiency of the catalyst can be enhanced. Hereupon, the conditions for putting the mixture in the state of high temperature (heating conditions) differ according to the kind of the acid as used and are therefore not limited. The conditions will do, for example, if they are such that the mixture is maintained in the temperature range of 40 to 100° C. for 0.5 to 5 hours.

The method (2) may further include another step besides the step (B) which needs the aforementioned steps (I) to (III). For example, the method (2) can include such as the step of removing the acid from the mixture resultant from the aforementioned step (III). By this removal step, the catalyst can be recovered as a solid by removing the acid from the mixture resultant from the aforementioned step (III). This solid can, as it is, be recycled for the reaction between the (meth)acrylic acid and the alkylene oxide. Incidentally, there is no limitation on the means of removing the acid from the aforementioned mixture. For example, conventional means such as reduced-pressure distillation and spray-drying are adoptable.

<Method (3)>:

The method (3) is a method in which the catalyst-recovering step includes the step of obtaining a residue as left behind distilling off the objective hydroxyalkyl (meth)acrylate from the resultant reaction liquid, with the method further comprising the step of replenishing the resultant residue with a fresh catalyst to use the resultant mixture for the next reaction.

In this method, the above distillation and replenishment may be applied not only to the reaction liquid as obtained as a result of the end of the predetermined reaction, but also to the reaction liquid in any stage after the beginning of the reaction, and then the resultant liquid may be used for the next reaction. In other words, there is no limitation on when how long time has passed since the beginning of the aforementioned reaction, the above distillation and replenishment should be applied to the reaction liquid to use the resultant liquid for the next reaction. Such as its timing can fitly be selected and can optionally be set so that there can be more enhanced such as the catalytic efficiency and the yield of the objective product.

As is mentioned above, in the method (3), the catalyst as used for the reaction is a catalyst including: a catalyst in the residue which is left behind distilling off the objective product and which contains the catalyst as has been used for the reaction; and a catalyst which is newly replenished. Incidentally, the above residue may be referred to as distillation residue or boiler residue and, generally, it is often liquid (e.g. tarry). Therefore, the above residue may be referred to as residual reaction liquid in the explanation of the method (3). However, it is herein provided that: the above residue should not be limited to such, but, in the case where the residue is obtained in a solid state without flowability, such a residue should also be included conceptually.

The mode for replenishing the above residual reaction liquid with the fresh catalyst may, for example, be such that: the catalyst is used for the next reaction after the fresh catalyst has beforehand been dissolved into the residual reaction liquid; or the fresh catalyst is dissolved into the residual reaction liquid after the next reaction has started; or only a portion of the fresh catalyst is beforehand dissolved into the residual reaction liquid, and then the remaining fresh catalyst is dissolved into the residual reaction liquid after the next reaction has started; or the fresh catalyst is beforehand dissolved into a portion of the residual reaction liquid, and then the rest of the residual reaction liquid is added after the next reaction has started. There is no especial limitation to these modes. Of the above, however, a favorable mode is that the entire fresh catalyst to be replenished is beforehand dissolved into the entire residual reaction liquid that is used for the next reaction, and then the resultant mixture is used for the next reaction, because such a mode involves no complicated operations and also facilitates the handling of the catalyst that is used for the next reaction.

Favorable examples of the above fresh catalyst include the same as previously cited as examples of the catalyst usable in the present invention production process.

The above residual reaction liquid is not limited to that from which the objective hydroxyalkyl (meth)acrylate has completely been distilled off. The objective hydroxyalkyl (meth)acrylate may remain more or less. In addition, the residual reaction liquid contains the catalyst as has been used for the reaction, but may further contain another component such as by-products and residual raw compounds. However, if possible, it is favorable that the above by-products and residual raw compounds are such as distilled off so as not to be contained, similarly to the hydroxyalkyl (meth)acrylate.

In the method (3), as to the above residual reaction liquid, after being replenished with the fresh catalyst, the entire amount may be used for the next reaction, or only a portion may be used, and also it may be used in the form optionally divided into portions for one or more kinds of reactions. There is no limitation if at least a portion of the catalyst as once used for the reaction can be used as the reaction catalyst again.

The amount of the above fresh catalyst as replenished is favorably in the range of 0.2 to 0.8 times, more favorably 0.3 to 0.7 times, still more favorably 0.4 to 0.6 times, of the amount (weight) of the catalyst as contained in the residual reaction liquid that is used for the next reaction. In the case where the above replenishing amount is smaller than 0.2 times, there is a possibility that the amount of formed impurities may increase, for example, because the reactivity (reaction efficiency) is so low as to prolong the reaction time too much. In the case where the above replenishing amount is larger than 0.8 times, there is a possibility that the amount of the fresh catalyst as replenished may be too large to desire more effects, so there may occur economical disadvantages. In addition, when the amount of the fresh catalyst as replenished is zero time, namely, when the next reaction is carried out with only the catalyst as contained in the residual reaction liquid, then there is a possibility that the danger of explosion may increase, for example, because the reactivity (reaction efficiency) more decreases to increase the amount of the alkylene oxide remaining in a reaction vessel at the end of the supply of the alkylene oxide. In addition, there is also a possibility that the amount of formed impurities may increase, for example, because the reaction rate is so slow as to prolong the reaction time.

In the method (3), the total of the amount (weight) of the catalyst in the residual reaction liquid that is used for the next reaction and the amount (weight) of the fresh catalyst with which the residual reaction liquid is replenished corresponds to the amount of the catalyst as used for the reaction. However, this amount as used is favorably adjusted so as to satisfy the aforementioned range of the amount of the catalyst as used in the present invention production process.

(Effects and Advantages of the Invention):

The present invention production process can provide a novel production process for a hydroxyalkyl (meth)acrylate in which: the diffusion of harmful substances due to disposal of catalysts can be reduced; and also the amount of the catalyst as used can be greatly saved in the entire production process.

DETAILED DESCRIPTION OF THE PREFERRED EMBODIMENTS

Hereinafter, the present invention is more specifically illustrated by the following examples of some preferred embodiments in comparison with comparative examples not according to the invention. However, the invention is not limited to these examples in any way. Incidentally, hereinafter, for convenience, the unit "liter(s)" may be referred to simply as "L". In addition, the units "weight %" and "volume %" may be referred to as "wt %" and "vol %" respectively.

PRODUCTION EXAMPLE

A SUS-316-made autoclave of 1 L in capacity having a stirrer was charged with 448 g of methacrylic acid, 0.90 g of chromium acetate as a catalyst, and 0.45 g of phenothiazine as a polymerization inhibitor. Air in the autoclave was displaced with nitrogen, and thereafter the contents of the autoclave were heated to 60° C., and then the internal pressure was adjusted to 0.1 MPa. Subsequently, 252 g of ethylene oxide was supplied into the autoclave at an almost constant rate over a period of 4 hours, while the reaction temperature was maintained at 60° C., thus carrying out a reaction. After the end of the supply of the ethylene oxide, the reaction temperature was raised to 80° C. to continue the reaction until the amount of the unreacted methacrylic acid as measured by neutralization titration decreased to 0.10 wt %. As a result of this continuation of the reaction for 2.1 hours, the amount of the unreacted methacrylic acid decreased to 0.10 wt %. Therefore the resultant reaction liquid was cooled. The reaction liquid as obtained was analyzed by gas chromatography. As a result, it was found that: the concentration of hydroxyethyl methacrylate that was the objective product was 96.0 wt %, and the concentration of ethylene glycol dimethacrylate that was a diester was 0.08 wt %, and the concentration of diethylene glycol monomethacrylate that was a diaddition product was 3.7 wt %, and the concentration of hydroxyethyl acetate was 0.3 wt %.

Subsequently, the entire reaction liquid as obtained was charged into a SUS-316-made distillation boiler of 1 L in capacity, and 0.14 g of methylhydroquinone was further added thereto, and then the bottom of the distillation boiler was heated in an oil bath to carry out distillation batchwise. As to the distillation conditions then, while the absolute pressure and the temperature were adjusted to 4 hPa and 80-100° C. respectively and further while air was introduced into the boiler at 300 mL/hour, the distillation was carried out over a period of 4 hours, thus obtaining 630 g of a condensed liquid (purified product) and 70 g of a residue. Incidentally, the purified product as obtained was analyzed by gas chromatography. As a result, its purity was found to be 98 wt %.

EXAMPLE 1-1

A SUS-316-made vessel of 500 mL in capacity having a stirrer was charged with: 70 g of the residue, as obtained in Production Example 1; 13 g of strongly acidic cation-exchange resin (product name: PK-208, produced by Mitsubishi Chemical Corporation); and 50 g of methanol. Then, the resultant mixture was stirred at 80° C. for 4 hours. As a result, the color of the solution, containing the residue, changed from dark green to light green.

Hereupon, the chromium ion concentration in the above solution decreased from 4,500 ppm (before stirring) to 120 ppm (after stirring). Also, 97.3 wt % of the chromium acetate, as contained in the residue, was adsorbed to the strongly acidic cation-exchange resin.

EXAMPLE 1-2

There was carried out the same procedure as of Example 1-1 except that strongly basic anion-exchange resin (product name: SA-12, produced by Mitsubishi Chemical Corporation) was used instead of the strongly acidic cation-exchange resin. As a result, the chromium ion concentration in the solution, containing the residue, decreased from 4,500 ppm (before stirring) to 300 ppm (after stirring). Also, 93.3 wt % of the chromium acetate, as contained in the residue, was adsorbed to the strongly basic anion-exchange resin.

COMPARATIVE EXAMPLE 1-1

There was carried out the same procedure as of Example 1-1 except that the stirring at 80° C. was changed to the stirring at 50° C. As a result, the chromium ion concentration in the solution, containing the residue, decreased from 4,500 ppm (before stirring) to 1,035 ppm (after stirring). Also, 77.0 wt % of the chromium acetate, as contained in the residue, was adsorbed to the strongly acidic cation-exchange resin.

COMPARATIVE EXAMPLE 1-2

There was carried out the same procedure as of Example 1-1 except that the stirring at 80° C. was changed to the stirring at 25° C. As a result, the chromium ion concentration in the solution, containing the residue, decreased from 4,500 ppm (before stirring) to 2,340 ppm (after stirring). Also, 48.0 wt % of the chromium acetate, as contained in the residue, was adsorbed to the strongly acidic cation-exchange resin.

EXAMPLE 2-1

A SUS-316-made vessel of 300 mL in capacity having a stirrer was charged with 70 of the residue as obtained in Production Example 1, and 100 g of 5 wt % aqueous sodium hydroxide solution was added thereto, and then the resultant mixture was stirred at 60° C. for 1 hour. As a result, a white insoluble product precipitated in the liquid. Subsequently, this insoluble product was filtrated and thereafter washed twice with 5 g of ion-exchanged water, thus obtaining a white powder. Next, the white powder as obtained was charged into a glass-made flask of 50 mL in capacity, and 5 g of acetic acid was added thereto, and the resultant mixture was stirred at 90° C. for 1 hour. As a result, the white powder dissolved to form a dark green liquid. Thereafter, the dark green liquid as obtained was pressure-reduced to an absolute pressure of 100 hPa to distill the acetic acid off under the reduced pressure, thus obtaining 0.85 g of a dark green powder. The resultant dark green powder was analyzed by elemental analysis and IIk analysis. As a result, it was found that the above dark green powder was chromium acetate. The recovery ratio of the chromium acetate was 94.4 wt %.

Next, the reaction between the methacrylic acid and the ethylene oxide was carried out in the same way as of Production Example 1 except to use 0.9 g of the above obtained dark green powder instead of 0.90 g of the chromium acetate that was used as the catalyst in Production Example 1. As a result, the continuation of the reaction for 2.1 hours decreased the amount of the unreacted methacrylic acid to 0.10 wt %. Therefore the resultant reaction liquid was cooled. The reaction liquid as obtained was analyzed by gas chromatography. As a result, it was found that: the concentration of hydroxyethyl methacrylate that was the objective product was 96.0 wt %, and the concentration of ethylene glycol dimethacrylate that was a diester was 0.08 wt %, and the concentration of diethylene glycol monomethacrylate that was a diaddition product was 3.7 wt %, and the concentration of hydroxyethyl acetate was 0.3 wt %.

EXAMPLE 2-2

An amount of 0.68 g of a dark green powder was obtained in the same way as of Example 2-1 except that: 100 g of 5 wt % ammonia water was used instead of 100 g of 5 wt % aqueous sodium hydroxide solution, and the number of times of the washing with 5 g of ion-exchanged water after the filtration was changed to once. The resultant dark green powder was analyzed in the same way as of Example 2-1. As a result, it was found that the above dark green powder was chromium acetate. The recovery ratio of the chromium acetate was 75.6 wt %.

Next, the reaction between the methacrylic acid and the ethylene oxide was carried out in the same way as of Production Example 1 except to use 0.9 g of the above obtained dark green powder instead of 0.90 g of the chromium acetate that was used as the catalyst in Production Example 1. As a result, the continuation of the reaction for 2.1 hours decreased the amount of the unreacted methacrylic acid to 0.10 wt %. Therefore the resultant reaction liquid was cooled. The reaction liquid as obtained was analyzed by gas chromatography. As a result, it was found that: the concentration of hydroxyethyl methacrylate that was the objective product was 96.0 wt %, and the concentration of ethylene glycol dimethacrylate that was a diester was 0.08 wt %, and the concentration of diethylene glycol monomethacrylate that was a diaddition product was 3.7 wt %, and the concentration of hydroxyethyl acetate was 0.3 wt %.

EXAMPLE 2-3

An amount of 0.50 g of a dark green powder was obtained in the same way as of Example 2-1 except that: 100 g of ion-exchanged water was used instead of 100 g of 5 wt % aqueous sodium hydroxide solution, and the number of times of the washing with 5 g of ion-exchanged water after the filtration was changed to once. The resultant dark green powder was analyzed in the same way as of Example 2-1. As a result, it was found that the above dark green powder was chromium acetate. The recovery ratio of the chromium acetate was 55.6 wt %.

Next, the reaction between the methacrylic acid and the ethylene oxide was carried out in the same way as of Production Example 1 except to use 0.9 g of the above obtained dark green powder instead of 0.90 g of the chromium acetate that was used as the catalyst in Production Example 1. As a result, the continuation of the reaction for 2.1 hours decreased the amount of the unreacted methacrylic acid to 0.10 wt %. Therefore the resultant reaction liquid was cooled. The reaction liquid as obtained was analyzed by gas chromatography. As a result, it was found that: the concentration of hydroxyethyl methacrylate that was the objective product was 96.0 wt %, and the concentration of ethylene glycol dimethacrylate that was a diester was 0.08 wt %, and the concentration of diethylene glycol monomethacrylate that was a diaddition product was 3.7 wt %, and the concentration of hydroxyethyl acetate was 0.3 wt %.

EXAMPLE 2-4

A white powder was obtained in the same way as of Example 2-1. Next, the white powder as obtained was charged into a glass-made flask of 50 mL in capacity, and 5 g of methacrylic acid was added thereto, and the resultant mixture was stirred at 90° C. for 1 hour. As a result, the white powder dissolved to form a dark green liquid. The dark green liquid as obtained was pressure-reduced to an absolute pressure of 100 hPa to distill the methacrylic acid off under the reduced pressure. As a result, 1.05 g of a dark green powder was obtained. The resultant dark green powder was analyzed by elemental analysis and IR analysis. As a result, it was found that the above dark green powder was chromium methacrylate. From the above results, it was found that the dark green liquid was a liquid containing the chromium methacrylate in an amount of 20 wt %. The recovery ratio of the chromium acetate (the recovery ratio as calculated by converting the chromium methacrylate into the chromium acetate) was 94.0 wt %.

Next, the reaction between the methacrylic acid and the ethylene oxide was carried out in the same way as of Production Example 1 except that: 5.4 g of the above-obtained dark green liquid was used instead of 0.90 g of the chromium acetate that was used as the catalyst in Production Example 1, and the amount of the methacrylic acid was changed to 443 g. As a result, the continuation of the reaction for 2.2 hours decreased the amount of the unreacted methacrylic acid to 0.10 wt %. Therefore the resultant reaction liquid was cooled. The reaction liquid as obtained was analyzed by gas chromatography. As a result, it was found that: the concentration of hydroxyethyl methacrylate that was the objective product was 96.0 wt %, and the concentration of ethylene glycol dimethacrylate that was a diester was 0.08 wt %, and the concentration of diethylene glycol monomethacrylate that was a diaddition product was 3.7 wt %, and the concentration of hydroxyethyl acetate was 0.1 wt %.

COMPARATIVE EXAMPLE 2-1

The reaction between the methacrylic acid and the ethylene oxide was carried out in the same way as of Production Example 1 except that 70 g of the residue as obtained in Production Example 1 was, as it was, used instead of 0.90 g of the chromium acetate that was used as the catalyst in Production Example 1. However, the results were as follows. The reaction temperature was raised to 80° C., and thereafter the reaction was continued for 4 hours, but the amount of the unreacted methacrylic acid decreased merely to 30 wt %, so the reaction did not progress entirely.

EXAMPLE 3-1

(Residual Reaction Liquid):

A SUS-316-made autoclave of 1.5 L in capacity having a stirrer was charged with 572 g of acrylic acid, 3.81 g of fresh chromium acetate as a catalyst, and 0.48 g of hydroquinone monomethyl ether as a polymerization inhibitor.

The contents of the autoclave were heated to 50° C., and thereafter air in the autoclave was displaced with nitrogen, and then the oxygen concentration and the internal pressure were adjusted to 3 vol % and 0.05 MPa respectively.

Thereafter, 367 g of ethylene oxide was supplied into the above autoclave at a constant rate over a period of 4 hours, while the reaction temperature was maintained at 50° C.

After the end of the supply of the ethylene oxide, the reaction temperature was raised to 70° C. to continue the reaction.

As a result of this continuation of the reaction for 3 hours, the unreacted acrylic acid decreased to not more than 0.10 wt %. Therefore the reaction was finished and then the resultant reaction liquid was cooled.

Subsequently, 900 g of the reaction liquid as obtained by the above reaction was charged into a SUS-316-made distillation boiler of 1.0 L in capacity, and thereto 0.14 g of hydroquinone monomethyl ether was added as a polymerization inhibitor.

The distillation boiler was heated in an oil bath to carry out distillation batchwise. As to the distillation conditions, while the internal pressure of the distillation boiler and the temperature of the oil bath were adjusted to 3 hPa and 65–80° C. respectively and further while air was introduced into the distillation boiler at 250 mL/hour, the distillation was carried out.

This distillation distilled off hydroxyethyl acrylate that was the objective product, so that there were obtained 786 g of a purified product (distillated product) and 108 g of a residue (which is hereinafter referred to as residual reaction liquid (1)).

The concentration of the chromium acetate in the residual reaction liquid (1) as obtained was 3.37 wt %.

(Production Process Utilizing the Residual Reaction Liquid):

A SUS-316-made autoclave of 1.5 L in capacity having a stirrer was charged with 572 g of acrylic acid, 85 g of the residual reaction liquid (1) (chromium acetate content: 2.86 g), 1.67 g of fresh chromium acetate as a catalyst, and 0.48 g of hydroquinone monomethyl ether as a polymerization inhibitor.

The contents of the autoclave were heated to 70° C., and thereafter air in the autoclave was displaced with nitrogen, and then the oxygen concentration and the internal pressure were adjusted to 3 vol % and 0.05 MPa respectively.

Thereafter, 367 g of ethylene oxide was supplied into the above autoclave at a constant rate over a period of 4 hours, while the reaction temperature was maintained at 70° C.

At the end of the supply of the ethylene oxide, the composition of the reaction liquid was such that the acrylic acid and the ethylene oxide were 15.5 wt % and 9.73 wt % respectively, and the conversion of the acrylic acid was 74.2 mol %. In addition, at that time, the ethylene oxide concentration and the oxygen concentration in the gas phase portion of the autoclave were 21 vol % and 2.8 vol % respectively.

After the end of the supply of the ethylene oxide, the reaction was continued while the reaction temperature was left constant at 70° C. When 4 hours had passed, the concentration of the unreacted acrylic acid decreased to not more than 0.1 wt %. Therefore the resultant reaction liquid was cooled. The concentration of ethylene glycol diacrylate and the concentration of diethylene glycol monoacrylate in the reaction liquid as obtained were 0.29 wt % and 6.7 wt % respectively.

EXAMPLE 3-2

(Residual Reaction Liquid):

A SUS-316-made autoclave of 1.5 L in capacity having a stirrer was charged with 572 g of acrylic acid, 3.81 g of fresh chromium acetate as a catalyst, and 0.48 g of hydroquinone monomethyl ether as a polymerization inhibitor.

The contents of the autoclave were heated to 50° C., and thereafter air in the autoclave was displaced with nitrogen, and then the oxygen concentration and the internal pressure were adjusted to 3 vol % and 0.05 MPa respectively.

Thereafter, 367 g of ethylene oxide was supplied into the above autoclave at a constant rate over a period of 4 hours, while the reaction temperature was maintained at 50° C.

At the same time as the end of the supply of the ethylene oxide, the reaction was finished, and then the resultant reaction liquid was cooled.

At the end of the cooling, the composition of the reaction liquid was such that the acrylic acid and the ethylene oxide were 20.1 wt % and 12.9 wt % respectively.

Subsequently, 900 g of the reaction liquid as obtained by the above reaction was charged into a SUS-316-made distillation boiler of 1.0 L in capacity, and thereto 0.14 g of hydroquinone monomethyl ether was added as a polymerization inhibitor.

The distillation boiler was heated in an oil bath to carry out distillation batchwise. As to the distillation conditions, while the internal pressure of the distillation boiler and the temperature of the oil bath were adjusted to 3 hPa and 65–80° C. respectively and further while air was introduced into the distillation boiler at 250 mL/hour, the distillation was carried out.

This distillation distilled off hydroxyethyl acrylate that was the objective product, so that there were obtained 552 g of a purified product (distillated product) and 234 g of a residue (which is hereinafter referred to as residual reaction liquid (2)).

The concentration of the chromium acetate in the residual reaction liquid (2) as obtained was 1.55 wt %.

(Production Process Utilizing the Residual Reaction Liquid):

A SUS-316-made autoclave of 1.5 L in capacity having a stirrer was charged with 572 g of acrylic acid, 185 g of the residual reaction liquid (2) (chromium acetate content: 2.87 g), 1.67 g of fresh chromium acetate as a catalyst, and 0.48 g of hydroquinone monomethyl ether as a polymerization inhibitor.

The contents of the autoclave were heated to 70° C., and thereafter air in the autoclave was displaced with nitrogen, and then the oxygen concentration and the internal pressure were adjusted to 3 vol % and 0.05 MPa respectively.

Thereafter, 367 g of ethylene oxide was supplied into the above autoclave at a constant rate over a period of 4 hours, while the reaction temperature was maintained at 70° C.

At the end of the supply of the ethylene oxide, the composition of the reaction liquid was such that the acrylic acid and the ethylene oxide were 13.8 wt % and 9.36 wt % respectively, and the conversion of the acrylic acid was 77.3 mol %. In addition, at that time, the ethylene oxide concentration and the oxygen concentration in the gas phase portion of the autoclave were 20 vol % and 2.8 vol % respectively.

After the end of the supply of the ethylene oxide, the reaction was continued while the reaction temperature was left constant at 70° C. When 4 hours had passed, the concentration of the unreacted acrylic acid decreased to not more than 0.1 wt %. Therefore the resultant reaction liquid was cooled. The concentration of ethylene glycol diacrylate and the concentration of diethylene glycol monoacrylate in the reaction liquid as obtained were 0.26 wt % and 6.5 wt % respectively.

COMPARATIVE EXAMPLE 3-1

There was carried out the same procedure as of Example 3-1 except not to charge the residual reaction liquid (1).

At the end of the supply of the ethylene oxide, the composition of the reaction liquid was such that the acrylic acid and the ethylene oxide were 18.4 wt % and 12.5 wt % respectively, and the conversion of the acrylic acid was 69.3 mol %. In addition, at that time, the ethylene oxide concentration and the oxygen concentration in the gas phase portion of the autoclave were 25 vol % and 2.8 vol % respectively. Similarly to Example 3-1, the gas composition deviated from the explosion range.

After the end of the supply of the ethylene oxide, the reaction was continued while the reaction temperature was left constant at 70° C. When 4 hours had passed, the composition of the resultant reaction liquid was confirmed. As a result, it was such that: the concentration of the unreacted acrylic acid, the concentration of the ethylene glycol diacrylate, and the concentration of diethylene glycol monoacrylate were 3.6 wt %, 0.42 wt %, and 7.42 wt % respectively.

In comparison with Example 3-1, after the same reaction time had passed, the concentration of the unreacted acrylic acid was higher and also the amount of formed impurities was larger.

COMPARATIVE EXAMPLE 3-2

There was carried out the same procedure as of Example 3-1 except not to charge the fresh (unused) chromium acetate.

At the end of the supply of the ethylene oxide, the composition of the reaction liquid was such that the acrylic acid and the ethylene oxide were 29.2 wt % and 19.6 wt % respectively, and the conversion of the acrylic acid was 51.4 mol %. In addition, at that time, the ethylene oxide concentration and the oxygen concentration in the gas phase portion of the autoclave were 36 vol % and 2.8 vol % respectively. This gas composition was within the explosion range, so there occurred danger of explosion. Thus, the reaction was continued after it had been confirmed that there was no ignition source nearby.

After the end of the supply of the ethylene oxide, the reaction was continued while the reaction temperature was left constant at 70° C. When 4 hours had passed, the composition of the resultant reaction liquid was confirmed. As a result, it was such that: the concentration of the unreacted acrylic acid, the concentration of the ethylene glycol diacrylate, and the concentration of diethylene glycol monoacrylate were 13.1 wt %, 0.34 wt %, and 9.48 wt % respectively.

In comparison with Example 3-1, after the same reaction time had passed, the concentration of the unreacted acrylic acid was higher and also the amount of formed impurities was larger.

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A production process for a hydroxyalkyl (meth)acrylate, which comprises the step of carrying out a reaction between (meth) acrylic acid and an alkylene oxide in the presence of a catalyst in order to produce the hydroxyalkyl (meth) acrylate;

with the production process further comprising the step of recovering the catalyst as has been used for the reaction; and wherein the catalyst-recovering step includes the step of causing a cation-exchange resin to adsorb the catalyst as contained in a residue as left behind after distilling off the objective hydroxyalkyl (meth)acrylate from the resultant reaction liquid.

2. A production process according to claim 1, wherein the adsorption is carried out under mixing of the residue, the ionexchange resin, and a polar solvent.

3. A production process for a hydroxyalkyl (meth)acrylate, which comprises the step of carrying out a reaction between (meth)acrylic acid and an alkylene oxide in the presence of a catalyst in order to produce the hydroxyalkyl (meth) acrylate;

with the production process further comprising the step of recovering the catalyst as has been used for the reaction; and wherein the catalyst-recovering step includes the step of mixing a solid with an acid, wherein the solid is a product obtained by applying solid-liquid separation to a mixture of the resultant reaction liquid and/or its residue with water and/or an alkali solution, wherein the residue is a residue as left behind after distilling off the objective hydroxyalkyl (meth)acrylate from the reaction liquid.

4. A production process according to claim 3, wherein: the mixture of the reaction liquid and/or its residue with the water and/or alkali solution is put in a state of high temperature of 40 to 100° C.; and/or the resultant mixture of the solid and the acid is put in a state of high temperature of 40 to 100° C.

5. A production process for a hydroxyalkyl (meth)acrylate, which comprises the step of carrying out a reaction between (meth) acrylic acid and an alkylene oxide in the presence of a catalyst in order to produce the hydroxyalkyl (meth) acrylate;

with the production process further comprising the step of recovering the catalyst as has been used for the reaction; and wherein the catalyst-recovering step includes the step of obtaining a residue as left behind after distilling off the objective hydroxyalkyl (meth)acrylate from the resultant reaction liquid, with the production process further comprising the step of replenishing the resultant residue with a fresh catalyst to use the resultant mixture for the next reaction.

6. A production process according to any one of claims 1 to 5, wherein the catalyst is a chromium compound.

* * * * *